(12) United States Patent
Hogan et al.

(10) Patent No.: US 7,153,919 B2
(45) Date of Patent: Dec. 26, 2006

(54) USE OF SULFUR CONTAINING INITIATORS FOR ANIONIC POLYMERIZATION OF MONOMERS

(75) Inventors: Terrence E. Hogan, Akron, OH (US); William Hergenrother, Akron, OH (US); Yuan-Yong Yan, Copley, OH (US); David Lawson, Uniontown, OH (US)

(73) Assignee: Bridgestone Corporation, Tokyo (JP)

( * ) Notice: Subject to any disclaimer, the term of this patent is extended or adjusted under 35 U.S.C. 154(b) by 0 days.

(21) Appl. No.: 10/533,408

(22) PCT Filed: Oct. 30, 2003

(86) PCT No.: PCT/US03/34597

§ 371 (c)(1),
(2), (4) Date: Apr. 29, 2005

(87) PCT Pub. No.: WO2004/041870

PCT Pub. Date: May 21, 2004

(65) Prior Publication Data

US 2006/0030657 A1    Feb. 9, 2006

Related U.S. Application Data

(60) Provisional application No. 60/455,508, filed on Mar. 18, 2003, provisional application No. 60/422,461, filed on Oct. 30, 2002.

(51) Int. Cl.
*C08F 36/04* (2006.01)
*C08F 4/48* (2006.01)

(52) U.S. Cl. .................. 526/335; 526/173; 526/178; 526/180; 526/181; 526/340; 525/105; 525/272; 525/313; 525/370; 525/371; 525/375; 524/52; 524/436; 524/437; 524/445; 524/571

(58) Field of Classification Search ............... 526/173, 526/178, 180, 181, 335, 340; 525/105, 272, 525/313, 375, 370, 371; 524/52, 436, 437, 524/445, 571

See application file for complete search history.

(56) References Cited

U.S. PATENT DOCUMENTS 3,699,191 A * 10/1972 Niemann .................. 525/272
4,429,091 A    1/1984 Hall ......................... 526/181
4,616,069 A   10/1986 Watanabe et al. ........... 525/370
5,496,940 A    3/1996 Lawson et al. ............. 540/450
5,502,131 A    3/1996 Antkowiak et al. ......... 526/180
6,720,391 B1   4/2004 Schwindeman et al. .... 525/355

FOREIGN PATENT DOCUMENTS

| EP | 1016674 | 7/2000 |
|---|---|---|
| EP | 709408 | 8/2001 |
| WO | 01/49695 | 7/2001 |
| WO | 04/041870 | 5/2004 |

OTHER PUBLICATIONS

"Polymerization of Vinyl Monomers by Alkali Metal-Thiobenzophenone Complexes", Yuji Minoura and Sadao Tsuboi, Journal Of Polymer Science: Part A-1 vol. 8, 125-138 (1970).

"A Convenient High Yield Synthesis of Functional Methacrylates via Dethioacetalization. Synthesis of Methacrylate S,S-Acetal Derivatives as Intermediates", Florence Caye et al., Phosphorus, Sulfur and Silicon, vol. 143, 197-220 (1998).

"Organosulfur Chemistry. 3. NMR Spectra of Carbanions Derived from 1, 3-Dithianes as Related to the High Stereoselectivity in their Reactions with Electrophiles", Anthony G. Abatjoglou et al., Journal of the American Chemical Society, Dec. 7, 1977.

"Synthesis of Symmetrical and Unsymmetrical 2,5-Bis(trialkylsilyl)furans and 2,6-Bis(trialkylsilyl)-4H-pyrans from 1,4- and 1,5-Bis(acylsilanes)", Jean-Philippe Bouillon et al., Synthesis 2000, No. 6, 843-849, Sep. 26, 1999.

"Protonation and Methylation of Conformationally Fixed 2-Lithio-1, 3-dithianes. Some Reactions of Remarkable Stereoselectivity", A. A. Hartman et al., Journal of the American Chemical Society, vol. 93, 2572-3 (1971).

* cited by examiner

*Primary Examiner*—Fred Teskin
(74) *Attorney, Agent, or Firm*—Meredith Palmer; Arthur M. Reginelli

(57) ABSTRACT

An initiator is presented for anionically polymerizing monomers, to provide a functional head group on the polymer. A polymer having a functional head group derived from a sulfur containing anionic initiator, and optionally as additional functional group resulting from the use of a functional terminating reagent, coupling agent or linking agent is also provided. A method is presented for anionically polymerizing monomers comprising the step of polymerizing the monomers with a sulfur containing anionic initiator to provide a functional head group on the polymer. An elastomeric compound, comprising a functional polymer and filler is also described. Also provided is a tire having decreased rolling resistance resulting from a tire component containing a vulcanizable elastomeric compound.

20 Claims, No Drawings

USE OF SULFUR CONTAINING INITIATORS FOR ANIONIC POLYMERIZATION OF MONOMERS

This application claims the priority of U.S. Provisional Ser. No. 60/422,461 filed on Oct. 30, 2002 and U.S. Provisional Ser. No. 60/455,508 filed on Mar. 18, 2003.

FIELD OF THE INVENTION

This invention relates to functionalized polymers and rubber vulcanizates prepared therefrom.

BACKGROUND OF THE INVENTION

In the art of making tires, it is desirable to employ rubber vulcanizates that demonstrate reduced hysteresis loss, i.e., less loss of mechanical energy to heat. Hysteresis loss is often attributed to polymer free ends within the cross-linked rubber network, as well as the disassociation of filler agglomerates.

Functionalized polymers have been employed to reduce hysteresis loss and increase bound rubber. The functional group of the functionalized polymer is believed to reduce the number of polymer free ends. Also, the interaction between the functional group and the filler particles reduces filler agglomeration, which thereby reduces hysteretic losses attributable to the disassociation of filler agglomerates (i.e. Payne effect).

Selection of certain functionalized anionic-polymerization initators can provide a polymer product having functionality at the head of the polymer chain. A functional group can also be attached to the tail end of an anionically polymerized polymer by terminating a living polymer with a functionalized compound.

Conjugated diene monomers are often anionically polymerized by using organometallic compounds as initiators. Exemplary organometallics that are well-known as anionic-polymerization initiators for diene monomers, with and without monovinyl aromatic monomers, include alkyl-lithium, trialkyltin lithium, and certain aminolithium compounds. The synthesis of lithiodithiane reagents is known as is there addition to conjugated ketones. However, no use of sulfur containing initiators, particularly lithium thio acetal based compounds, is known for anionic polymerization of dienes, trienes, monovinyl aromatics or combinations thereof.

Because functionalized polymers are advantageous, especially in the preparation of tire compositions, there exists a need for additional functionalized polymers. Moreover, because precipitated silica has been increasingly used as a reinforcing particulate filler in tires, functionalized elastomers having an affinity to both carbon black and silica fillers are needed.

SUMMARY OF THE INVENTION

In general, the present invention advances the art by providing a new organometallic anionic polymerization initiators for polymerizing diene, triene or monovinyl aromatic monomers, and combinations thereof.

The present invention also provides a method for anionically polymerizing monomers comprising the step of polymerizing the monomers with a sulfur containing anionic initiator to provide a functional head group on the polymer.

The present invention also provides a polymer having a sulfur containing functional head group.

The present invention also provides a rubber composition having a sulfur containing functionalized polymer.

The present method further provides a pneumatic tire having at least one component comprising a rubber compound containing a polymer having a head group derived from a sulfur containing anionic initiator.

The functionalized polymers of this invention advantageously provide carbon black, carbon black/silica, and silica filled rubber vulcanizates having reduced hysteresis loss.

DETAILED DESCRIPTION OF ILLUSTRATIVE EMBODIMENTS

The present invention provides sulfur containing lithio compounds, including lithio alkyl thio acetals and lithio aryl thio acetals, as initiators for anionically polymerizing dienes, trienes, monovinyl aromatics and combinations thereof. Suitable sulfur containing lithio compounds have the general formula

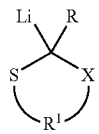

where R is selected from $C_1$ to $C_6$ trialkyl-silyl groups, $C_1$ to $C_{20}$ alkyl groups, $C_4$ to $C_{20}$ cycloalkyl groups, $C_6$ to $C_{20}$ aryl groups, thienyl, furyl, and pyridyl groups; and R may optionally have attached thereto any of following functional groups: $C_1$ to $C_{10}$ alkyl groups, $C_6$ to $C_{20}$ aryl groups, $C_2$ to $C_{10}$ alkenyl groups, $C_3$ to $C_{10}$ non-terminal alkynyl groups, ethers, tert-amines, oxazolines, thiazolines, phosphines, sulfides, silyls, and mixtures thereof, where $R^1$ is selected from the group consisting of $C_2$ to $C_8$ alkylene groups and where X is selected from the group consisting of S, O and NR, wherein R is as defined above, and may optionally have attached thereto any of the above identified functional groups.

The sulfur containing lithio compounds having a tert-amine functional group of the present invention have the general formula:

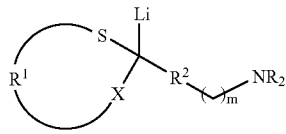

where $R^2$ is selected from the group consisting of $C_1$ to $C_8$ alkylene groups, $C_3$ to $C_{12}$ cycloalkylene groups and $C_6$ to $C_{18}$ arylene groups; m is 0 to about 8; and R, $R^1$ and X are as defined above.

A preferred lithio alkyl thio acetal initiator is 2-lithio-2-methyl-1,3-dithiane which can be represented as follows:

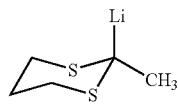

A preferred lithio aryl thio acetal initiator is 2-lithio-2-phenyl-1,3-dithiane (PDT-Li). Its structure can be represented as follows:

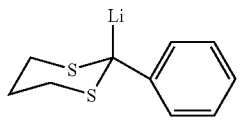

Other exemplary initiators of the present invention include:

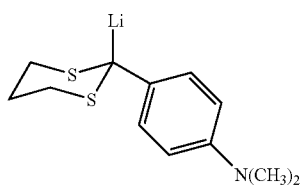

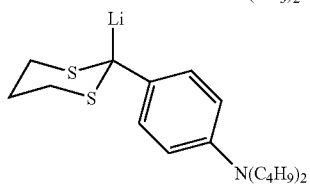

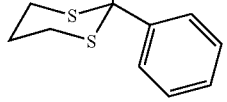

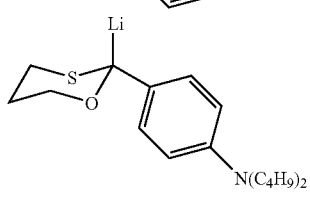

The initiators of the present invention may be prepared by reacting an initiator precursor compound with an organolithium compound, such as, n-butyllithium. These initiator precursors have the general formula:

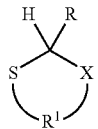

where R, $R^1$ and X are as defined hereinabove.

As with the sulfur containing lithio compounds defined above, the initiator precursors may also have attached to the R group any of following functional groups: $C_1$ to $C_{10}$ alkyl groups, $C_6$ to $C_{20}$ aryl groups, $C_2$ to $C_{10}$ alkenyl groups, $C_3$ to $C_{10}$ non-terminal alkynyl groups, ethers, tert-amines, oxazolines, thiazolines, phosphines, sulfides, silyls, and mixtures thereof. These functionalized precursor compounds can then be reacted with an organolithium compound to form a functionalized sulfur containing lithio initiator.

Several representative species of functionalized precursors are as follows:

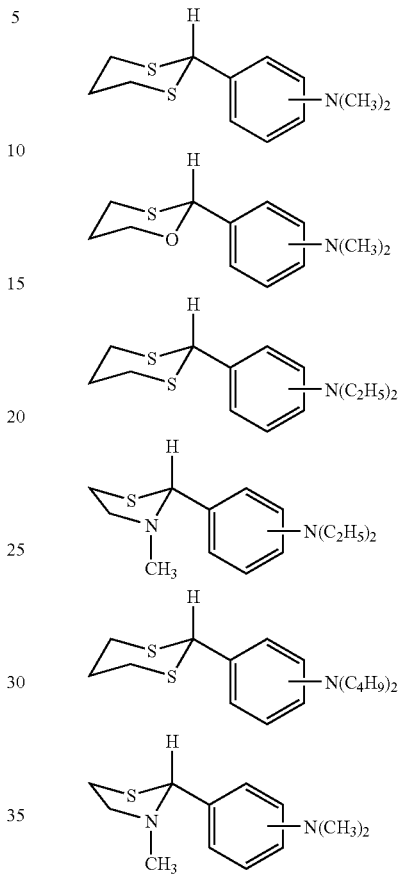

For a comprehensive summary of known functionalized phenyls, see the article "Recent advance in living anionic polymerization of functionalized styrene derivatives", by Hirao et al, *Prog. Polym. Sci.* (2002) 1399–1471, Elsevier, the subject matter of which is incorporated herein by reference.

A non-limiting example of the synthesis of sulfur functionalized initiators, specifically 2-lithio-2-methyl-1,3-dithiane and 2-lithio-2-phenyl-1,3-dithiane, from an initiator precursor and organolithium compound prior to polymerization is as follows: commercially available solutions of 2-methyl-1,3-dithiane or 2-phenyl-1,3-dithiane are added to dried tetrahydrofluran, and cooled to approximately −78° C. A solution comprising butyllithium and hexane is then added thereto. The resulting solution is then stirred for approximately 3 hours and allowed to stand overnight at a temperature of less than about 10° C. The resulting solutions may then be used to initiate anionic polymerization. This type of initiator preparation may occur in any appropriate reaction vessel, including a polymerization reactor, prior to the addition of a monomner(s) solution.

Depending on the stability of the initiator precursor, it may be desirable to prepare the initiator in situ, as opposed to preparing and storing said precursor. The dithiane initiators of the present invention can be synthesized in situ in a solution comprising the monomer or monomers to be polymerized. Generally, the in situ preparation of anionic initiator is practiced by creating a solution comprising a polymerization solvent, and the monomer(s) to be polymerized. This first solution is generally heated to about −80° C. to about 100° C., and more preferably from about −40° C. to about 50° C., and most preferable from about 0° C. to about 25° C., and the non-lithiated initiator precursor and organolithium are added thereto. The solution is then heated to a temperature within the range of about −80° C. to about 150° C., and more preferably from about 25° C. to about 120° C. and most preferably from about 50° C. to about 100° C. and allowed to react for a period of time of from about 0.02 hours to about 168 hours, more preferably from about 0.08 hours to about 48 hours, and most preferably from about 0.16 hours to about 2 hours, or as sufficient to result in the formation of a solution (cement) containing the desired functional polymer. Reaction times and temperatures may vary as necessary to allow the precursor and organolithium to react, and subsequently polymerize the monomer solution.

A non-limiting example of an in-situ initiator synthesis involves creating a solution comprising hexane, styrene monomer, and butadiene. This first solution is heated to about 24° C. and 2-methyl-1,3-dithiane and butyllithium are added thereto. The solution is then heated to approximately 54° C. and allowed to react for approximately 40 minutes.

The initiators of the present invention are useful for functionalizing an anionically polymerized living polymer. These functionalized polymers are formed by reacting a ftmctionalized anionic initiator with certain unsaturated monomers to propagate a polymeric structure. The functionalized polymer may be defied by the formula

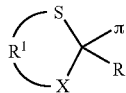

where R is selected from $C_1$ to $C_6$ trialkyl-silyl groups, $C_1$ to $C_{20}$ alkyl groups, $C_4$ to $C_{20}$ cycloalkyl groups, $C_6$ to $C_{20}$ aryl groups, thienyl, furyl, and pyridyl groups; and R may optionally have attached thereto any of the following functional groups: $C_1$ to $C_{10}$ alkyl groups, $C_6$ to $C_{20}$ aryl groups, $C_2$ to $C_{10}$ alkenyl groups, $C_3$ to $C_{10}$ non-terminal alkynyl groups, ethers, tert-amines, oxazolines, thiazolines, phosphines, sulfides, silyls, and mixtures thereof; where $R^1$ is selected from $C_2$ to $C_8$ alkylene groups, where X is selected from S, O and NR, where R is defined above, and may optionally have attached thereto any of the above identified functional groups and where it is a polymer chain.

Throughout the formation propagation of the polymer, the polymeric structure is anionic and "living." A new batch of monomer subsequently added to the reaction can add to the living ends of the existing chains and increase the degree of polymerization. A living polymer, therefore, is a polymeric segment having a living or reactive end. Anionic polymerization is further described in George Odian, *Principles of Polymerization*, ch. 5 (3rd Ed. 1991), or Panek, 94 J. Am. Chem. Soc., 8768 (1972), which are incorporated herein by reference.

The sulfur containing lithio alkyl thio acetals and sulfur containing lithio aryl thio acetals can be used as anionic polymerization initiators in amounts varying widely based upon the desired polymer characteristics. In one embodiment it is preferred to employ from about 0.1 to about 100, and more preferably from about 0.33 to about 10 mmol of lithium per 100 g of monomer.

Monomers that can be employed in preparing an anionically polymerized living polymer include any monomer capable of being polymerized according to anionic polymerization techniques. These monomers include those that lead to the formation of elastomeric homopolymers or copolymers. Suitable monomers include, without limitation, conjugated $C_4$–$C_{12}$ dienes, $C_4$–$C_{12}$ monovinyl aromatic monomers and $C_6$–$C_{20}$ trienes. Examples of conjugated diene monomers include, without limitation, 1,3-butadiene, isoprene, 1,3-pentadiene, 2,3-dimethyl-1,3-butadiene, and 1,3-hexadiene. A non-limiting example of trienes includes myrcene. Aromatic vinyl monomers include, without limitation, styrene, alpha-methyl styrene, p-methylstyrene, and vinylnapthalene. When preparing elastomeric copolymers, such as those containing conjugated diene monomers and aromatic vinyl monomers, the conjugated diene monomers and aromatic vinly monomers are normally used at a ratio of 95:5 to 50:50, and preferable 95:5 to 65:35.

Anionic polymerizations are typically conducted in a polar solvent, such as tetrahydrofuran (THF), or a non-polar hydrocarbon, such as the various cyclic and acyclic hexanes, heptanes, octanes, pentanes, their alkylated derivatives, and mixtures thereof, as well as benzene.

In order to promote randomization in copolymerization and to control vinyl content, a polar coordinator may be added to the polymerization ingredients. Amounts range between 0 and 90 or more equivalents per equivalent of lithium. The amount depends on the amount of vinyl desired, the level of styrene employed and the temperature of the polymerization, as well as the nature of the specific polar coordinator (modifier) employed. Suitable polymerization modifiers include for example, ethers, or amines to provide the desired microstructure and randomization of the comonomer units.

Compounds useful as polar coordinators include those having an oxygen or nitrogen heteroatom and a non-bonded pari of electrons. Examples include dialkyl ethers of mono and oligo alkylene glycols; "crown" ethers; tertiary amines such as tetramethylethylene diamine (TMEDA); linear THF oligomers; and the like. Specific examples of compounds useful as polar coordinators include tetrahydrofuran (THF), linear and cyclic oligomeric oxolanyl alkanes such as 2,2-bis(2'-tetrahydrofuryl)propane, dipiperidyl ethane, dipiperidyl methane, hexamethylphosphoramide, N-N'-dimethylpiperazine, diazabicyclooctane, dimethyl ether, diethyl ether, tributylamine and the like. The linear and cyclic oligomeric oxolanyl alkane modifiers are described in U.S. Pat. No. 4,429,091, incorporated herein by reference.

To terminate the polymerization, and thus further control polymer molecular weight, a terminating agent, coupling agent or linking agent may be employed, all of these agents being collectively referred to herein as "terminating reagents". Useful terminating, coupling or linking agents include active hydrogen compounds such as water or alcohol. Certain of these reagents may provide the resulting polymer with multifunctionality. That is, the polymers initiated according to the present invention, may carry the functional head group as discussed hereinabove, and may also carry a second functional group as a result of the terminating reagents, coupling agents and linking agents used in the polymer synthesis.

Useful functional terminating reagents are those disclosed in U.S. Pat. Nos. 5,502,131, 5,496,940 and 4,616,069, the subject matters of which are incorporated herein by reference, and include tin tetrachloride, $(R)_3SnCl$, $(R)_2SnCl_2$, $RSnCl_3$, carbodiimides, N-cyclic amides, N,N' disubstituted cyclic ureas, cyclic amides, cyclic ureas, isocyanates, Schiff bases, 4,4'-bis(diethylamino)benzophenone, alkyl thiothiazolines, carbon dioxide and the like. Other agents include the alkoxy silanes $Si(OR)_4$, $RSi(OR)_3$, $R_2Si(OR)_2$ cyclic siloxanes and, mixtures thereof. The organic moiety R is selected from the group consisting of alkyls having from 1 to about 20 carbon atoms, cycloalkyls having from about 3 to about 20 carbon atoms, aryls having from about 6 to about 20 carbon atoms and aralkyls having from about 7 to about 20 carbon atoms. Typical alkyls include n-butyl, s-butyl, methyl, ethyl, isopropyl and the like. The cycloalkyls include cyclohexyl, menthyl and the like. The aryl and the aralkyl groups include phenyl, benzyl and the like. Preferred endcapping agents are tin tetrachloride, tributyl tin chloride, dibutyl tin dichloride, tetraethylorthosilicate and 1,3-dimethyl-2-imidazolidinone (DMI). The foregoing listing of terminating reagents is not to be construed as limiting but rather as enabling. While a terminating reagent can be employed, practice of the present invention is not limited to a specific reagent or class of such compounds.

While terminating to provide a functional group on the terminal end of the polymer is preferred, it is further preferred to terminate by a coupling reaction, with for example, tin tetrachloride or other coupling agent such as silicon tetrachloride ($SiCl_4$), esters and the like.

Anionically polymerized living polymers can be prepared by either batch, semi-batch or continuous methods. A batch polymerization is begun by charging a blend of monomer(s) and normal alkane solvent to a suitable reaction vessel, followed by the addition of the polar coordinator (if employed) and an initiator compound. The reactants are heated to a temperature of from about 20 to about 130° C. and the polymerization is allowed to proceed for from about 0.1 to about 24 hours. This reaction produces a reactive polymer having a reactive or living end. Preferably, at least about 30% of the polymer molecules contain a living end. More preferably, at least about 50% of the polymer molecules contain a living end. Even more preferably, at least about 80% contain a living end.

A continuous polymerization is begun by charging monomer(s), initiator and solvent at the same time to a suitable reaction vessel. Thereafter, a continuous procedure is followed that removes the product after a suitable residence time and replenishes reactants.

In a semi-batch polymerization the reaction medium and initiator are added to a reaction vessel, and the monomer(s) is continuously added over time at a rate dependent on temperature, monomer/intiator/modifier concentrations, etc. Unlike a continuous polymerization, the product is not continuously removed from the reactor.

Molecular weight of the polymers prepared using the initiators of the present invention can be determined by number average molecular weight ($M_n$) and weight average molecular weight ($M_w$). For polybutadiene polymers, $M_n$ values range from about 0.5 kg/mol to about 500 kg/mol. For copolymers, such as SBR, $M_n$ values range from about 0.5 kg/mol to about 500 kg/mol.

After formation of the functional polymer, a processing aid and other optional additives such as oil can be added to the polymer cement. The functional polymer and other optional ingredients are then isolated from the solvent and preferably dried. Conventional procedures for desolventization and drying may be employed. In one embodiment, the functional polymer may be isolated from the solvent by steam desolventization or hot water coagulation of the solvent followed by filtration. Residual solvent may be removed by using conventional drying techniques such as oven drying or drum drying. Alternatively, the cement may be directly drum dried.

The functionalized polymers, and rubber compositions containing such functionalized polymers, of this invention are particularly useful in preparing tire components. These tire components can be prepared by using the functionalized polymers of this invention alone or together with other rubbery polymers. Other rubbery elastomers that may be used include natural and synthetic elastomers. The synthetic elastomers typically derive from the polymerization of conjugated diene monomers. These conjugated diene monomers may be copolymerized with other monomers such as vinyl aromatic monomers. Other rubbery elastomers may derive from the polymerization of ethylene together with one or more alpha-olefins and optionally one or more diene monomers.

Useful rubbery elastomers include natural rubber, synthetic polyisoprene, polybutadiene, polyisobutylene-co-isoprene, neoprene, poly(ethylene-co-propylene), poly(styrene-co-butadiene), poly(styrene-co-isoprene), poly(styrene-co-isoprene-co-butadiene), poly(isoprene-co-butadiene), poly(ethylene-co-propylene-co-diene), polysulfide rubber, acrylic rubber, urethane rubber, silicone rubber, epichlorohydrin rubber, and mixtures thereof These elastomers can have a myriad of macromolecular structures including linear, branched and star shaped. Preferred elastomers include neural rubber, isoprene, styrene-butadiene copolymers, and butadiene rubber because of their common usage in the tire industry.

The rubber compositions may include fillers such as inorganic and organic fillers. The organic fillers include carbon black and starch. The inorganic fillers may include silica, aluminum hydroxide, magnesium hydroxide, clays (hydrated aluminum silicates), and mixtures thereof Preferred fillers are carbon black, silica and mixtures thereof.

The elastomers can be compounded with all forms of carbon black alone, or in a mixture with silica. The carbon black can be present in amounts ranging from about 0 to about 100 phr, with about five to about 80 phr being preferred. When both carbon black and silica are employed in combination as the reinforcing filler, they are often used in a carbon black-silica ratio of about 10:1 to about 1:4.

The carbon blacks can include any of the commonly available, commercially-produced carbon blacks, but those having a surface area (EMSA) of at least 20 $m^2/g$ and, more preferably, at least 35 $m^2/g$ up to 200 $m^2/g$ or higher are preferred. Surface area values used in this application are determined by ASTM D-1765 using the cetyltrimethylammonium bromide (CTAB) technique. Among the useful carbon blacks are furnace black, channel blacks and lamp blacks. More specifically, examples of useful carbon blacks include super abrasion furnace (SAF) blacks, high abrasion furnace (HAF) blacks, fast extrusion furnace (FEF) blacks, fine furnace (FF) blacks, intermediate super abrasion furnace (ISAF) blacks, semi-reinforcing furnace (SRF) blacks, medium processing channel blacks, hard processing channel blacks and conducting channel blacks. Other carbon blacks which can be utilized include acetylene blacks. A mixture of two or more of the above blacks can be used in preparing the carbon black products of the invention. The carbon blacks utilized in the preparation of the vulcanizable elastomeric compositions of the invention can be in pelletized form or an unpelletized flocculent mass. Preferably, for more uniform mixing, unpelletized carbon black is preferred.

Examples of suitable silica reinforcing filler include, but are not limited to, precipitated amorphous silica, wet silica (hydrated silicic acid), dry silica (anhydrous silicic acid), fumed silica, calcium silicate, and the like. Other suitable fillers include aluminum silicate, magnesium silicate, and the like. Among these, precipitated amorphous wet-process, hydrated silicas are preferred. These silicas are so-called precipitated because they are produced by a chemical reaction in water, from which they are precipitated as ultrafine, spherical particles. These primary particles strongly associate into aggregates, which in turn combine less strongly into agglomerates. The surface area, as measured by the BET method gives the best measure of the reinforcing character of different silicas. For silicas of interest for the present invention, the surface area should be about 32 $m^2/g$ to about 400 $m^2/g$, with the range of about 100 $m^2/g$ to about 250 $m^2/g$ being preferred, and the range of about 150 $m^2/g$ to about 220 $m^2/g$ being most preferred. The pH of the silica filler is generally about 5.5 to about 7 or slightly over, preferably about 5.5 to about 6.8.

Silica can be employed in the amount of about 0 to about 100 phr, preferably in an amount of about 5 to about 80 phr and, more preferably, in an amount of about 30 to about 80 phr. The useful upper range is limited by the high viscosity imparted by fillers of this type, Some of the commercially available silicas which can be used include, but are not limited to, Hi-Sil® 190, Hi-Sil® 210, Hi-Sil® 215, Hi-Sil® 233, Hi-Sil® 243, and the like, produced by PPG Industries (Pittsburgh, Pa.). A number of useful commercial grades of different silicas are also available from Degussa Corporation (e.g., VN2, VN3), Rhone Poulenc (e.g., Zeosil® 1165MP), and J.M. Huber Corporation.

The elastomeric compounds of the invention can optionally further include a silica coupling agent such as, but not limited to, a mercaptosilane, a bis(trialkoxysilylorgano)polysulfide, a 3-thiocyanatopropyl trimethoxysilane, or the like, or any of the silica coupling agents that are known to those of ordinary skill in the rubber compounding art. Exemplary mercaptosilanes include, but are not limited to, 1-mercaptomethyltriethoxysilane, 2-mercaptoethyltriethoxysilane, 3-mercaptopropyltriethoxysilane, 3-mercaptopropylmethyl-diethoxysilane, 2-mercaptoethyltriproxysilane, 18-mercaptooctadecyldiethoxychlorosilane, and the like. Exemplary bis(trialkoxysilylorgano)polysulfide silica coupling agents include, but are not limited to, bis(3-triethoxysilyl-propyl)tetrasulfide (TESPT), which is sold commercially under the tradename Si69 by Degussa Inc., New York, N.Y., and bis(3-triethoxysilylpropyl)disulfide (TESPD) or Si75, available from Degussa, or Silquest® A1589, available from Crompton. The polysulfide organosilane silica coupling agent can be present in an amount of about 0.01% to about 20% by weight, based on the weight of the silica, preferably about 0.1% to about 15% by weight, and especially about 1% to about 10%.

Compounding involving silica fillers is also disclosed in U.S. Pat. Nos. 6,221,943, 6,342,552, 6,348,531, 5,916,961, 6,252,007, 6,369,138, 5,872,176, 6,180,710, 5,866,650, 6,228,908 and 6,313,210, the disclosures of which are incorporated by reference herein.

The elastomeric compositions are compounded or blended by using mixing equipment and procedures conventionally employed in the art, such as mixing the various vulcanizable polymer(s) with reinforcing fillers and commonly used additive materials such as, but not limited to, curing agents (for a general disclosure of suitable vulcanizing agents one can refer to Kirk-Othmer, *Encyclopedia of Chemical Technology*, 3rd ed., Wiley Interscience, N.Y. 1982, Vol. 20, pp. 365–468, particularly "Vulcanization Agents and Auxiliary Materials" pp. 390–402), activators, retarders and accelerators; processing additives, such as oils; resins, including tackifying resins; plasticizers; pigments; additional fillers; fatty acid; zinc oxide; waxes; antioxidants; antiozonants; peptizing agents; and the like. As known to those skilled in the art, the additives mentioned above are selected and commonly used in conventional amounts. For example, without limitation, a tire component compound typically contains elastomers, fillers, processing oilslaids, antidegradants, zinc oxide, stearic acid, sulfur, accelerators and coupling agents. Such compounds can have such additional ingredients in the following amounts:

fillers: from about 0 to about 150 phr, and preferably from about 30 to about 80 phr;

processing oils/aids: from about 0 to about 75 phr, and preferably from about 0 to about 40 phr;

antidegradants: from about 0 to about 10 phr, and preferably from about 0 to about 5 phr;

stearic acid: from about 0 to about 5 phr, and preferably from about 0 to about 3 phr;

zinc oxide: from about 0 to about 10 phr, and preferably from about 0 to about 5 phr;

sulfur: from about 0 to about 10 phr, and preferably from about 0 to about 4 phr;

accelerators: from about 0 to about 10 phr, and preferably from about 0 to about 5 phr, and coupling agent: from about 0 to about 30 phr, and preferably from about 5 to about 15 phr.

Preferably, an initial master batch is prepared that includes the rubber component and the reinforcing fillers, as well as other optional non-curative additives, such as processing oil, antioxidants, and the like. After the master batch is prepared, one or more optional remill stages can follow in which either no ingredients are added to the first mixture, or the remainder of the non-curing ingredients are added, in order to reduce the compound viscosity and improve the dispersion of the reinforcing filler. The final step of the mixing process is the addition of vulcanizing agents to the mixture.

The resulting elastomeric compounds when vulcanized using conventional rubber vulcanization conditions exhibit reduced hysteresis properties and are particularly adapted for use as tread rubbers for tires having reduced rolling resistance.

Further embodiments of the invention are described in the following examples.

GENERAL EXPERIMENTAL TESTING PROCEDURES

Molecular Weight Determination: Molecular weights were measured by gel permeation chromatography (GPC) using a Waters Model 150-C instrument equipped with a Model 2414 Refractometer and a Model 996 Photodiode Array Detector (UV). Molecular weights were calculated from a universal calibration curve based on polystyrene standards and corrected using the following Mark-Houwink constants for SBR: $k=0.000269$, $\alpha=0.73$.

Styrene and Vinyl Content and Small Molecule Structure Confirmation: Styrene and vinyl content, and small molecule structure confirmation were determined using $^1$H-NMR (CDCl$_3$) and $^{13}$C NMR measurements on a 300 MHz Gemini 300 NMR Spectrometer System (Varian).

Glass Transition Temperature ($T_g$): The glass transition temperature was determined using a DSC 2910 Differential Scanning Calorimeter (TA Instruments). The $T_g$ was determined as the temperature where an inflection point occurred in the heat capacity ($C_p$) change.

Dynamic Mechanical Properties: The dynamic mechanical properties were measured using two techniques. A Rheometrics Dynamic Analyzer RDAII (Rheometric Scientific) in the parallel plate mode was used with 15 mm thick, 9.27 mm diameter buttons. The loss modulus, G", storage modulus, G', and tan δ were measured over deformation of 0.25–14.5% at 1 Hz and 50° C. The Payne Effect was estimated by calculating the difference of G' (0.25% E)–G' (14.0% E). A RDA700 (Rheometric Scientific) in the torsion rectangular mode was also used with samples having the dimensions 31.7 mm×12.7 mm×2.0 mm. The temperature was increased at a rate of 5° C. min$^{-1}$ from −80° C. to 100° C. The moduli (G' and G") were obtained using a frequency of 5 Hz and a deformation of 0.5% from −80° C. to −10° C. and 2% from −10° C. to 100° C.

Mooney Viscosity: Mooney viscosity measurements were conducted according to ASTM-D 1646-89.

Tensile: The tensile mechanical properties were measured according to ASTM-D 412 (1998) Method B at 25° C. The tensile test specimens are rings with a dimension of 1.27 mm width and 1.90 mm thick. A specific gauge length of 25.4 mm is used for the tensile test.

Cure: In the present invention, cure is measured utilizing moving die rheometer (MDR) according to ASTM D2084 (1995).

Bound Rubber: Bound rubber, a measure of the percentage of rubber bound, through some interaction to the filler, was determined by solvent extraction with toluene at room temperature. More specifically, a test specimen of each uncured rubber formulation was placed in toluene for 3 days. The solvent was removed and the residue was dried and weighed. The percentage of bound rubber was then determined according to the formula % bound rubber=$[100(w_d-F)]/R$ where $w_d$ is the weight of the dried residue, F is the weight of the filler and any other solvent insoluble matter in the original sample and R is the weight of rubber in the original sample.

Thin Layer Chromatography (TLC): TLC was done on Sigma-Aldrich TLC plates, silica gel on aluminum.

Column Chromatography: Column chromatography was conducted using silica gel sorbent (200~425 Mesh, Fisher Scientific).

GENERAL EXPERIMENTAL

In order to demonstrate practice of the present invention, the following examples have been prepared and tested.

A dried 28 oz (0.8 L) or 7 oz (0.2 L) glass bottle, which previously had been sealed with extracted septum liners and perforated crown caps under a positive nitrogen purge, was used for all of the preparations.

Dried butadiene in hexane (21 to 23 weight percent butadiene), dried styrene in hexane (styrene blend, 33 weight percent styrene), dried hexane, n-butyllithium (1.68 M in hexane), cyclic oligomeric oxolanyl alkane modifier in hexane (1.6 M solution in hexane, stored over calcium hydride), and butylated hydroxytoluene (BHT) solution in hexane were used. Tetrahydrofuran (THF) was distilled from potassium benzophenone ketyl.

Commercially available reagents and starting materials (Aldrich Chem. Co. and Fisher Scientific) include the following: 2-methyl-1,3-dithiane; 2-trimethylsilyl-1,3-dithiane; 2-methylthio-2-thiazoline; tetraethyl orthosilicate; 1-bromo-3-chloropropane; 2-phenyl-1,3-dithiane, benzaldehyde dimethyl acetal, 4-(dimethylamino)benzaldehyde; 4-(dibutylamino)benzaldehyde; 1,3-propanedithiol; 3-mercapto-1-propanol; 1,3-dimethyl-2-imidazolidinone (DMI); tributyltin chloride and tin(IV) chloride, which were used as purchased without further purification.

The examples should not, however, be viewed as limiting the scope of the invention. The claims will serve to define the invention.

EXAMPLES

Example No. 1

Synthesis of 2-lithio-2-methyl-1,3-dithiane

To a 0.8 L $N_2$ purged bottle equipped with a serum cap was added 350 mL of dried tetrahydrofuran and 10 mL of 2-methyl-1,3-dithiane (83.5 mmol). The bottle was cooled to −78° C. and 55.83 mL of 1.510 M butyllithium (84.3 mmol) in hexane was added. The reaction was stirred at −78° C. for 3 hours and then stored at −25° C. overnight. Titration of the resulting solution indicated that the solution contained 0.234 M active lithium compound. To elucidate the structure of this compound, the solution was added to a dried solution of 8.26 mL of 1-bromo-3-chloropropane (83.5 mmol) in 90 mL tetrahydrofuran at −78° C. After 3 hours, the products were examined by GC/MS and found to contain >95% 2-(3-chloropropyl)-2-methyl-1,3-dithiane. No 1-chloroheptane was observed indicating that the butyllithium had completely reacted with the 2-methyl-1,3-dithiane.

Example No. 2

Synthesis of Poly(styrene-cobutadiene) with 2-lithio-2-methyl-1,3-dithiane

To a 1.75 L $N_2$ purged reactor equipped with a stirrer was added 1.12 kg of hexane, 0.48 kg of 33 wt % styrene in hexane, and 2.89 kg of 22.0 wt % butadiene in hexane. The reactor was then heated to 24° C. and 0.5 mL of 1.6 M of a cyclic oligomeric oxolanyl alkane modifier, in hexane and 22.63 mL of 0.234 M 2-lithio-2-methyl-1,3-dithiane in tetrahydrofuran was charged to the reactor. The reactor jacket was then heated to 54° C. After 15 minutes, the batch temperature peaked at 76.5° C. After an additional 25 minutes, the cement was removed from the reactor, coagulated in isopropanol containing butylated hydroxy toluene (BHT), and drum dried to yield a polymer with the following properties: $M_n$=153 kg/mol, $M_w$=167 kg/mol, $T_g$=−44.4° C., 21.7% styrene, 1.3% block styrene, 32.1% vinyl, and 46.2% 1,4 butadiene incorporation.

Example No. 3

Synthesis of Poly(styrene-co-butadiene) with 2-lithio-2-methyl-1,3-dithiane

To a 1.75 L $N_2$ purged reactor equipped with a stirrer was added 1.12 kg of hexane, 0.48 kg of 33 wt % styrene in hexane, and 2.89 kg of 22.0 wt % butadiene in hexane. The reactor was then heated to 24° C. and 0.5 mL of 1.6 M of cyclic oligomeric oxolanyl alkane modifier in hexane and 16.96 mL of 0.234 M 2-lithio-2-methyl-1,3-dithiane in tetrahydrofuran was charged to the reactor. The reactor jacket was then heated to 54° C. After 17 minutes, the batch temperature peaked at 75.7° C. After an additional 10 minutes, the cement was removed from the reactor, coagulated in isopropanol containing butylated hydroxy toluene (BHT), and drum dried to yield a polymer with the following properties: $M_n$=208 kg/mol, $M_w$=240 kg/mol, $T_g$=−43.8° C., 22.2% styrene, 1.6% block styrene, 31.2% vinyl, and 46.5% 1,4 butadiene incorporation.

Example No. 4

Synthesis of Poly(styrene-co-butadiene) with in situ 2-lithio-2-methyl-1,3-dithiane To a 1.75 L $N_2$ purged reactor equipped with a stirrer was added 1.07 kg of hexane, 0.48 kg of 33 wt % styrene in hexane, and 2.95 kg of 21.6 wt % butadiene in hexane. The reactor was then heated to 24° C. and 0.5 mL of 1.6 M of cyclic oligomeric oxolanyl alkane modifier in hexane and 8.47 mL of 0.5 M 2-methyl-1,3-dithiane in hexane, and 3.42 mL of 1.55 M butyllithium in hexanes was charged to the reactor. The reactor jacket was then heated to 54° C. After 28 minutes, the batch temperature peaked at 68.6° C. After an additional 10 minutes, the cement was removed from the reactor, coagulated in isopropanol containing butylated hydroxy toluene (BHT), and drum dried to yield a polymer with the following properties: $M_n$=135 kg/mol, $M_w$=142 kg/mol, $T_g$=−56.6° C.

Comparative Example No. 5

Synthesis of Poly(styrene-co-butadiene) with butyllithium

To a 1.75 L $N_2$ purged reactor equipped with a stirrer was added 1.07 kg of hexane, 0.48 kg of 33 wt % styrene in hexane, and 2.95 kg of 21.6 wt % butadiene in hexane. The reactor was then heated to 24° C. and 0.5 mL of 1.6 M of cyclic oligomeric oxolanyl alkane modifier in hexane and 22.6 mL tetrahydrofuran and 3.42 mL 1.55 M butyllithium in hexane was charged to the reactor. The reactor jacket was then heated to 54° C. After 15 minutes, the batch temperature peaked at 71.2° C. After an additional 10 minutes, the cement was removed from the reactor, coagulated in isopropanol containing butylated hydroxy toluene (BHT), and drum dried to yield a polymer with the following properties: $M_n$=157 kg/mol, $M_w$=168 kg/mol, $T_g$=−42.5° C., 21.3% styrene, 1.1% block styrene, 33.8% vinyl, and 45.0% 1,4 butadiene incorporation.

Comparative Example No. 6

Synthesis of Poly(styrene-co-butadiene) with butyllithium

To a 1.75 L $N_2$ purged equipped with a stirrer was added 1.07 kg of hexane, 0.48 kg of 33 wt % styrene in hexane, and 2.95 kg of 21.6 wt % butadiene in hexane. The reactor was then heated to 24° C. and 0.5 mL of 1.6 M of cyclic oligomeric oxolanyl alkane modifier in hexane and 16.96 mL tetrahydrofuran and 2.56 mL 1.55 M butyllithium in hexane was charged to the reactor. The reactor jacket was then heated to 54° C. After 17 minutes, the batch temperature peaked at 75.5° C. After an additional 10 minutes, the cement was removed from the reactor, coagulated in isopropanol containing butylated hydroxy toluene (BHT), and drum dried to yield a polymer with the following properties: $M_n$=190 kg/mol, $M_w$=207 kg/mol, $T_g$=−44.0° C., 22.1% styrene, 1.3% block styrene, 32.1% vinyl, and 45.9% 1,4 butadiene incorporation.

Next, three polybutadiene examples were prepared, Nos. 7–9, using butyllithium (control), 2-litho-2-methyl-1,3-dithiane and 2-lithio-2-trimethylsilyl-1,3-dithiane initiators, both dithiane being prepared in situ.

Comparative Example No. 7

Synthesis of Control Polybutadiene Initiated by Butyllithium

To a 0.8 L nitrogen purged bottle equipped with a serum cap was added 0.47 mL of 1.6M butyl lithium in hexane. Then, 27.3 g of hexane and 272.7 g of 22.0% butadiene in hexane were added. The reaction was heated to 50° C. for 4 hours. The resulting polymer solution was coagulated in isopropanol containing butylated hydroxy toluene (BHT), and drum dried to yield a polymer with the following properties: $M_n$=88.2 kg/mol, $M_w$ 104.5 kg/mol, $M_w/M_n$=1.18, $T_g$=−94.2° C.

Example No. 8

Synthesis of Polybutadiene Initiated by in situ Generated 2-litho-2-methyl-1,3-dithiane To a 0.8 L nitrogen purged bottle equipped with a serum cap was added 0.59 mL of 0.5M 2-methyl-1,3-dithiane and 0.47 mL of 1.6M butyl lithium in hexane. Then, 27.3 g of hexane and 272.7 g of 22.0% butadiene in hexane were added. The reaction was heated to 50° C. for 4 hours. The resulting polymer solution was coagulated in isopropanol containing BHT, and drum dried to yield a polymer with the following properties: $M_n$=101.6 kg/mol, $M_w$ 127.5 kg/mol, $M_w/M_n$=1.26, $T_g$=−94.6° C.

Example No. 9

Synthesis of Polybutadiene Initiated by in situ Generated 2-lithio-2-trimethylsilyl-1,3-dithiane To a 0.8 L nitrogen purged bottle equipped with a serum cap was added 0.29 mL of 1.0M 2-trimethylsilyl-1,3-dithiane and 0.47 mL of 1.6M butyl lithium in hexane. Then, 27.3 g of hexane and 272.7 g of 22.0% butadiene in hexane were added. The reaction was heated to 50° C. for 4 hours. The resulting polymer solution was coagulated in isopropanol containing BHT and drum dried to yield a polymer with the following properties: $M_n$=81.9 kg/mol, $M_w$ 125.9 kg/mol, $M_w/M_n$=1.54, $T_g$=−93.9° C.

The three polybutadiene polymers were subsequently compounded with other ingredients to prepare vulcanizable elastomeric compounds. Component parts by weight, per 100 parts of rubber (phr) are set forth in Table I.

TABLE I

Vulcanizable Elastomeric Compounds

| | MASTERBATCH | | |
|---|---|---|---|
| | Compound Example 10 | Compound Example 11 | Compound Example 12 |
| Polymer Example 7 | 100 | 0 | 0 |
| Polymer Example 8 | 0 | 100 | 0 |
| Polymer Example 9 | 0 | 0 | 100 |
| Carbon Black | 50 | 50 | 50 |
| Wax and Aromatic Oil | 11.5 | 11.5 | 11.5 |
| Stearic Acid | 2 | 2 | 2 |
| Antioxidant | 1 | 1 | 1 |
| Total | 164.5 | 164.5 | 164.5 |

TABLE I-continued

Vulcanizable Elastomeric Compounds

FINAL MIX

|  | Example 10 | Example 11 | Example 12 |
|---|---|---|---|
| Initial | 164.5 | 164.5 | 164.5 |
| Accelerators | 1.2 | 1.2 | 1.2 |
| Zinc Oxide | 2 | 2 | 2 |
| Sulfur | 1.3 | 1.3 | 1.3 |
| Total | 169.0 | 169.0 | 169.0 |

The masterbatches were prepared by mixing the initial compounds in a 300 g Brabender mixer operating at 60 rpm and 133° C. First, the polymer (of Examples 7, 8 and 9, respectively) was placed in the mixer, and after 0.5 minutes, the remaining ingredients except the stearic acid were added. The stearic acid was then added after 3 minutes. The initial components were mixed for 5–6 minutes. At the end of mixing the temperature was approximately 165° C. Each sample was transferred to a mill operating at a temperature of 60° C., where it was sheeted and subsequently cooled to room temperature.

The final components were mixed by adding the masterbatch and the curative materials to the mixer simultaneously. The initial mixer temperature was 65° C. and it was operating at 60 rpm. The final material was removed from the mixer after 2.25 minutes when the material temperature was between 100 to 105° C. The finals were sheeted into Dynastat buttons and 6×6×0.075 inch (15×15×0.1875 cm) sheets. The samples were cured at 171° C. for 15 minutes in standard molds placed in a hot press.

The resulting elastomeric compounds of Example Nos. 10–12 were then subjected to physical testing, the results of which are reported in Table II.

TABLE II

Physical Properties of Compounded Stocks

| Property | Compound Example 10 (Control) | Compound Example 11 | Compound Example 12 |
|---|---|---|---|
| MH (kg-cm) | 0.73 | 1.02 | 1.09 |
| ML (kg-cm) | 15.92 | 17.54 | 15.8 |
| $TS_2$ (min) | 1.38 | 1.24 | 1.27 |
| 200% Modulus @23° C. (MPa) | 2.73 | 2.81 | 2.66 |
| $T_b$ @23° C. (MPa) | 11.89 | 14.42 | 13.95 |
| $E_b$ @23° C. (%) | 593.7 | 617.7 | 628.5 |
| tan δ 7% E, 65° | 0.234 | 0.188 | 0.195 |
| ΔG' (50° C.) (MPa)* | 2.120 | 1.746 | 1.680 |

*ΔG' = G' (@0.25% E) – G' (@14.5% E)

The data in Table II establishes a reduced tan δ (improved hysteresis) for the elastomeric compounds containing polymers carrying functional headgroups from the initiator (Compound Examples 11 and 12) compared to the control compound (Example 10) containing the polymer of Example No. 7. Note that both tan δ and ΔG' are lower that the control, Example 10, indicating that dithiane functionalized polymers interact with the fillers. The lower tan δ and ΔG' values also indicate that tires made with such rubber should have lower rolling resistance properties. The next set of examples demonstrates the use of lithio aryl thio acetals as initiators.

Example No. 13

Synthesis of 2-lithio-2-phenyl-1,3-dithiane

To a solution of 2-phenyl-1,3-dithiane (2.1 g, 10.69 mmol) in THF (5 mL) and cyclohexane (10 mL) was added n-BuLi (6.37 mL, 1.68 M in hexane) dropwise via a syringe at –78° C. The solution was stirred for an additional 3 hours at 0° C. The resulting 0.5 M 2-litho-2-phenyl-1,3-dithiane (abbreviated as PDT-Li) was used for anionic initiator for polymerizing butadiene and/or butadiene/styrene and stored in an inert atmosphere of nitrogen in a refrigerator.

Example No. 14

Synthesis of 2-phenyl-1,3-oxathiane

To an oven-dried 250 mL flask fitted with a magnetic stirring bar and reflux condenser was introduced 0.4 g of Montmorillonite KSF, 1.65 g (10.8 mmol) of benzaldehyde dimethyl acetal in 35 mL of THF, followed by 1.0 g (10.8 mmol) of 3-mecapto-1-propanol in 5 mL of THF. The mixture was refluxed under nitrogen for 12 hours. After cooling to room temperature and filtered, the filtrate was washed with saturated $NaHCO_3$ (2×20 mL), saturated NaCl (20 mL) and dried over $MgSO_4$ (anhydrous). The solvent was evaporated; a chromatograph using silica gel [elution with Hexane/$Et_2O$ (70/30)] was obtained on the residue, yielding 1.9 g (97%) of 2-phenyl-1,3-oxathiolane. $^1$H-NMR ($CDCl_3$): δ 1.74 (m, 1H), 2.11 (m, 1H), 2.82, (m, 1H), 3.22 (m, 1H), 3.81 (m, 1H), 4.35 (m, 1H), 5.80 (s, 1H), 7.36 (m, 3H), 7.49 (m, 2H). $^{13}$C-NMR ($CDCl_3$): δ 25.73, 29.26, 70.74, 126.19, 128.46, 128.53, 139.52.

Example No. 15

Synthesis of 2-lithio-2-phenyl-1,3-oxathiane

To a solution of 2-phenyl-1,3-oxathiane from Example No. 14, (1.0 g, 5.5 mmol) in THF (5.8 mL) and hexane (5 mL) was added n-BuLi (3.3 mL, 1.68 M in hexane) dropwise via a syringe at –78° C. The solution was stirred for an additional 3 hours at –5° C. The resulting 0.39 M 2-lithio-2-phenyl-1,3-oxathiane (abbreviated as POT-Li) was used as an anionic initiator for polymerizing butadiene and/or butadiene/styrene.

Example No. 16

Synthesis of Polybutadiene with 2-lithio-2phenyl-1,3-dithiane

Two 0.8 L bottles were charged with 163.6 g of hexane, and 136.4 g of butadiene blend (22 wt % in hexane). This was followed by 1.2 mL (Ex. 16A) and 0.55 mL (Ex. 16B) of PDT-Li (from Ex. No. 13) added to the separate bottles by syringe. The bottles were agitated and heated at 50° C. for 1.5 hours. The polymer cements were terminated with a small amount of 2-propanol, treated with 4 mL of BHT solution; worked up with 2-propanol, and dried under vacuum for 12 hours. It should be noted that due to the varying amounts of initiator used for Examples 16A and 16B, the resulting polymers had differing molecular weights, as seen in Table III.

TABLE III

| | Ex. No. | |
|---|---|---|
| | 16 | 16A |
| Initiator | PDT-Li | PDT-Li |
| Amount (mL) | 1.2 | 0.55 |
| $M_n$ (kg/mol) | 60.9 | 120.6 |
| $M_w/M_n$ | 1.07 | 1.05 |

Example No. 17

Synthesis of Polybutadiene with 2-lithio-2-phenyl-1,3-oxathiane

The preparation and the procedure used for Examples 16A and 16B were repeated, using of POT-Li (as prepared in Ex. No. 15) as initiator. The molecular weights of the polymers are listed hereinbelow. It should be noted that due to the varying amounts of initiator used for Examples 17A and 17B, the resulting polymers had differing molecular weights, as seen in Table IV.

TABLE IV

| | Ex. No. | |
|---|---|---|
| | 17 | 17A |
| Initiator | POT-Li | POT-Li |
| Amount (mL) | 0.96 | 0.70 |
| $M_n$ (kg/mol) | 99.4 | 126.9 |
| $M_w/M_n$ | 1.08 | 1.16 |

Example No. 18

Synthesis of Poly(styrene-co-butadiene) with 2-lithio-2-phenyl-1,3-dithiane

A 0.8 L bottle was charged with 190 g of hexane, 20 g of styrene blend, and 120 g of butadiene blend (22 wt % in hexane), then 0.61 mL of PDT-Li (Ex. No. 13) by syringe. The bottle was agitated and heated at 50° C. for 1.5 hours. The polymer cement was terminated with a small amount of 2-propanol, treated with 4 mL of BHT solution, worked up with 2-propanol and drum dried. $M_n$=135.8 kg/mol, $M_w/M_n$=1.1, $T_g$=−69° C.

Example No. 19

Synthesis of Polybutadiene with In Situ 2-lithio-2-phenyl-1,3dithiane

A 0.8 L bottle was charged with 162.4 g of hexane, 137.6 g of butadiene blend (21.8 wt % in hexane), and 0.075 g of 2-phenyl-1,3-dithiane, then 0.23 mL of n-BuLi (1.68 M in hexane) by syringe. The bottle was agitated and heated at 50° C. for 1.5 hours. The polymer cement was terminated with a small amount of 2-propanol, treated with 4 mL of BHT solution; worked up with 2-propanol, and dried under vacuum for 12 hours. Presence of the 2-phenyl-1,3-dithiane headgroup was confirmed by UV trace detector, set at 254 nm used with the GPC. $M_n$=94.4 kg/mol, $M_w/M_n$=1.22, $T_g$=−72.7° C.

Comparative Example No. 20

Synthesis of Polybutadiene with n-BuLi

The preparation and the procedure used in Example 19 were repeated, but without adding 2-phenyl-1,3-dithiane. The product was a conventional polybutadiene. $M_n$=80.2 kg/mol, $M_w/M_n$=1.06, $T_g$=−94° C.

Example No. 21

Synthesis of 2-(4-dimethylamino)phenyl-1,3-dithiane

To an oven-dried 500 mL flask fitted with a magnetic stirring bar and reflux condenser was introduced 6.89 g (46.2 mmol) of 4-(dimethylamino)benzaldehyde, 8.8 g (46.2 mmol) of p-toluenesulfonic acid monohydrate, and 180 mL of THF. The mixture was stirred for 10 minutes, and then 2.5 g of Montmorillonite KSF was added, followed by 5 g (46.2 mmol) of 1,3-propanedithiol in 30 mL of THF. The mixture was refluxed under nitrogen for 12 hours. After cooling to room temperature and filtered, the filtrate was washed with saturated $NaHCO_3$ (2×100 mL), saturated NaCl (100 mL) and dried over $MgSO_4$ (anhydrous). The solvent was evaporated; a chromatograph using silica gel [elution with Hexane/$Et_2O$ (85/15)] was obtained on the residue, yielding 10.5 g (95%) of 2-[4-(dimenthylamino)]-phenyl-1,3-dithiane. $^1$H-NMR ($CDCl_3$): δ 1.90 (m, 1H), 2.14 (m, 1H), 2.93, (s, 6H), 2.97 (m, 4H), 5.11 (s, 1H), 6.67 (m, 2H), 7.33 (m, 2H), $^{13}$C-NMR ($CDCl_3$): δ 25.12, 32.28, 40.46, 50.89, 112.28, 126.62, 128.46, 150.43.

Example No. 22

Synthesis of 2-lithio-2-(4-dimethylamino)phenyl-1,3-dithiane

To a solution of 2-(4-dimethylamino)phenyl-1,3-dithiane (as prepared in Example No. 21, 1.25 g, 5.22 mmol in THF (8 mL) and $Et_3N$ (1 mL)) was added n-BuLi (3.1 mL, 1.68 M in hexane) dropwise via a syringe at −78° C. The solution was stirred for an additional 4 hours at 0° C. The resulting 0.43 M 2-lithio-2-(4-dimethyl-amino)phenyl-1,3-dithiane (abbreviated as DAPDT-Li) was used as anionic initiator for polymerizing butadiene and/or butadiene/styrene and stored in an inert atmosphere of nitrogen in a refrigerator.

Example No. 23

Synthesis of Polybutadiene with 2-lithio-2-(4-dimethylamino)phenyl-1,3-dithiane

A 0.8 L bottle was charged with 180 g of hexane, and 152 g of butadiene blend (21.7 wt % in hexane), then 1.6 mL of DAPDT-Li (prepared in Example 22) was added by syringe. The bottle was agitated and heated at 50° C. for 1.5 hours. The polymer cement was terminated with a small amount of 2-propanol, treated with 5 mL of BHT solution; worked up with 2-propanol, and dried under vacuum for 12 hours.

Example No. 24

Synthesis of Polybutadiene with 2-lithio-2-(4-dimethylamino)phenyl-1,3-dithiane

The preparation and the procedure used in Example No. 23 were repeated, but using 1.0 mL of DAPDT-Li (prepared Example 22). All polymers were analyzed by GPC using styrene as the standard and in THF solution. The molecular weights of the polymers are listed below.

TABLE V

| | Example No. | |
|---|---|---|
| | 23 | 24 |
| Initiator | DAPDT-Li | DAPDT-Li |
| $M_n$ (kg/mol) | 53.0 | 96.3 |
| $M_w/M_n$ | 1.028 | 1.033 |

All polymers were confined by UV trace detector, set at 254 nm used with the GPC.

Example No. 25

Synthesis of Poly(styrene-co-butadiene) with 2-lithio-2-(4-dimethyl-amino)phenyl-1,3-dithiane A 0.8 L bottle was charged with 188 g of hexane, 20.18 g of styrene blend (32.7%), and 122 g of butadiene blend (22 wt % in hexane), then 0.7 mL of DAPDT-Li (prepared in Example 22) and 0.05 mL of cyclic oligomeric oxolanyl alkane modifier (1.6 M in hexane) were added by syringe. The bottle was agitated and heated at 50° C. for 1.5 hours. The polymer cement was terminated with a small amount of 2-propanol, treated with 5 mL of BHT solution, work up with 2-propanol, and drum dried. $M_n$=107.4 kg/mol, $M_w/M_n$=1.11, $T_g$=−37.39° C.

Example No. 26

Synthesis of Poly(styrene-co-butadiene) with Butyllithium

The procedure of Example No. 25 was repeated using an equivalent molar amount of n-butyllithium as the initiator. $M_n$=101.6 kg/mol, $M_w/M_n$=1.05, $T_g$=−41.2° C.

Example No. 27

Synthesis of Poly(styrene-co-butadiene) with 2-lithio-2-(4-dimethyl-amino)phenyl-1,3-dithiane A 0.8 L bottle was charged with 188 g of hexane, 20.18 g of styrene blend (32.7%), and 122 g of butadiene blend (22 wt % in hexane), then 1.0 mL of DAPDT-Li (prepared in Example 22) was added by syringe, but without addition of a modifier. The bottle was agitated and heated at 50° C. for 1.5 hours. The polymer cement was terminated with a small amount of 2-propanol, treated with 5 mL of BHT solution, work tip with 2-propanol, and drum dried. $M_n$=115.2 kg/mol, $M_w/M_n$=1.1 kg/mol, $T_g$=−51.08° C.

Example No. 28

Synthesis of Poly(styrene-co-butadiene) with 2-lithio-2-(4-dimethyl-amino)phenyl-1,3-dithiane Into a two gallon (7.6 L) $N_2$ purged reactor, equipped with a stirrer, was added 1.619 kg of hexane, 0.414 kg of 33 wt % styrene in hexane, and 2.451 kg of 22.2 wt % butadiene in hexane. The reactor was charged with 21 mL of 0.3 M of 2-lithio-2-(4-dimethylamino)phenyl-1,3-dithiane (abbreviated as DAPDT-Li) and 1.05 mL of cyclic oligomeric oxolanyl alkane modifier (1.6 M in hexane) and then heated to 24° C. The reactor jacket was then heated to 50° C. After 16 minutes, the batch temperature peaked at 66.7° C. After an additional 25 minutes, samples of the cement were removed from the reactor into dried 28-oz (0.8 L) glass bottles, and terminated with one of the following: tributyltin chloride (3.68 M abbreviated as DAPDT-SBR-SnBu3), 1,3-dimethyl-2-imidazolidinone (DMI, 9.14 M abbreviated as DAPDT-SBR-DMI), and isopropanol (abbreviated as DAPDT-SBR-H) at 50° C. bath for 30 minutes, respectively, coagulated in isopropanol containing butylated hydroxy toluene (BHT), and drum dried to yield polymers with following properties, as seen in Table VI:

TABLE VI

| | Example No. | | |
|---|---|---|---|
| | 28A | 28B | 28C |
| Description | DAPDT-SBR-H | DAPDT-SBR-DMI | DAPDT-SBR-SnBu3 |
| $M_n$ (kg/mol) | 110.0 | 66.0* | 110.0 |
| $M_w$ (kg/mol) | 122.0 | 84.9* | 120.0 |
| $T_g$ (° C.) | −36.8 | −37.0 | −36.8 |

*apparent $M_n$ and $M_w$ are low due to interaction of polymer with GPC columns.

Example No. 29

Synthesis of Poly(styrene-co-butadiene) with in-situ 2-lithio-2-(4-dimethyl-amino)phenyl-1,3-dithiane The foregoing polymer was also prepared in situ as follows. To a two gallon (7.6 L) $N_2$ purged reactor equipped with a stirrer was added 1.610 kg of hexane, 0.412 kg of 33 weight percent styrene in hexane, and 2.462 kg of 22.1 weight percent butadiene in hexane. The reactor was then charged a mixture of 1.36 g of 2-(4-dimethylamino)phenyl-1,3-dithiane in 10 mL of THF and 1 mL of triethylamine with 3.37 mL of n-BuLi (1.68 M) in hexane, and agitated at 24° C. for 5 to 10 minutes, then 1.5 mL of cyclic oligomeric oxolanyl modifies (1.6 M in hexane) was charged, and the reactor jacket was then heated to 50° C. After 16 minutes, the batch temperature peaked at 62.9° C. After an additional 15 minutes, the cement was removed from the reactor into dried 28 oz (0.8 L) glass bottles, terminated with 1,3-dimethyl-2-imidazolidinone (DMI, 9.14 M, abbreviated as DAPDT-SBR-DMI), and isopropanol (abbreviated as DAPDT-SBR-H) at 50° C. bath for 30 minutes, respectively, coagulated in isopropanol containing butylated hydroxy toluene (BHT), and drum dried to yield polymers with the following properties, as shown in Table VII:

TABLE VII

| | Example No. | |
|---|---|---|
| | 29A | 29B |
| Description | DAPDT-SBR-H | DAPDT-SBR-DMI |
| $M_n$ (kg/mol) | 123.0 | 83.0* |
| $M_w$ (kg/mol) | 135.0 | 94.0* |
| $T_g$ (° C.) | −34.3 | −34.7 |

*apparent $M_n$ and $M_w$ are low due to interaction of polymer with GPC columns The SBR polymer prepared according to Example No. 25 was utilized to prepare a vulcanizable elastomer, designated as Example No. 30. For comparison, a control polymer was prepared using n-butyllithium as the initiator, from Example No. 26, and was designated as Example No. 31 (Control). Both stocks contained carbon black as the reinforcing filler and the formulations are provided in Table IV. Amounts listed are presented by parts per hundred rubber (phr).

TABLE VIII

Carbon Black Formulation

|  | Generic Formulation | Compound Example 30 | Compound Example 31 |
|---|---|---|---|
| MASTERBATCH |  |  |  |
| Polymer | 100 |  |  |
| Polymer Example 25 |  | 100 |  |
| Polymer Example 26 |  |  | 100 |
| Carbon Black-N343 type | 55 | 55 | 55 |
| Wax | 1 | 1 | 1 |
| Antiozonant | 0.95 | 0.95 | 0.95 |
| ZnO | 2.5 | 2.5 | 2.5 |
| Stearic Acid | 2 | 2 | 2 |
| Processing Oil | 10 | 10 | 10 |
| Subtotal, Masterbatch (phr) | 171.45 | 171.45 | 171.45 |
| FINAL |  |  |  |
| Masterbatch | 171.45 | 171.45 | 171.45 |
| Sulfur | 1.3 | 1.3 | 1.3 |
| Accelerators | 1.9 | 1.9 | 1.9 |
| Total (phr) | 174.65 | 174.65 | 174.65 |

The two compounds from Table VIII, Example Nos. 30 and 31, were next cured and then subjected to physical testing, as set forth in Table IX, hereinbelow.

TABLE IX

|  | Compound Example 30 | Compound Example 31 |
|---|---|---|
| 171° C. MDR $t_{50}$ (min): | 3.02 | 2.92 |
| 171° C. MH-ML (kg-cm): | 16.9 | 20.9 |
| $ML_{1+4}$ @ 130° C.: | 21.8 | 27.1 |
| 300% Modulus @ 23° C. (Mpa): | 9.08 | 11.69 |
| Tensile Strength @ 23° C. (Mpa): | 15.73 | 16.17 |
| tan δ, 0° C., 0.5% E, 5 Hz: | 0.1688 | 0.1790 |
| tan δ, 50° C., 0.2% E, 5 Hz: | 0.2831 | 0.2355 |
| RDA 0.25–14% ΔG' (MPa): | 4.8917 | 4.2280 |
| tan δ, 50° C., 5.0% E, 1 Hz: | 0.2620 | 0.2108 |
| Bound Rubber (%): | 10.1 | 19.0 |

The SBR polymer prepared according to Example No. 25 was then utilized to prepare a vulcanizable elastomer with a combination of carbon black and silica as fillers, and designated as Example No. 32. For comparison, control polymer Example No. 26, prepared using n-butyl lithium as the initiator, was also used in the same carbon black/silica containing compound (as Example No. 33). The complete formulations are provided in Table X. Amounts listed are presented by parts per hundred rubber (phr).

TABLE X

Silica/Carbon Black Formulation

|  | Generic Formulation | Compound Example 32 | Compound Example 33 |
|---|---|---|---|
| MASTERBATCH |  |  |  |
| Polymer | 100 |  |  |
| Polymer Example 25 |  | 100 |  |
| Polymer Example 26 |  |  | 100 |
| Silica | 30 | 30 | 30 |
| Carbon Black | 35 | 35 | 35 |
| Antiozonant | 0.95 | 0.95 | 0.95 |
| Stearic Acid | 1.5 | 1.5 | 1.5 |
| LVA Oil | 10 | 10 | 10 |
| Remill |  |  |  |
| 60% Si75 on carrier | 4.57 | 4.57 | 4.57 |
| FINAL |  |  |  |
| ZnO | 2.5 | 2.5 | 2.5 |
| Sulfur | 1.7 | 1.7 | 1.7 |
| Accelerators | 2.0 | 2.0 | 2.0 |
| PVI | 0.25 | 0.25 | 0.25 |
| Total (phr) | 188.47 | 188.47 | 188.47 |

The resulting compounds, Example Nos. 32 and 33, were next cured and then subjected to physical testing, as set forth in Table XI, hereinbelow.

TABLE XI

|  | Compound Example 32 | Compound Example 33 |
|---|---|---|
| 171° C. MDR $t_{50}$ (min): | 6.49 | 8.37 |
| 171° C. MH-ML (kg-cm): | 26.27 | 23.00 |
| $ML_{1+4}$ @ 130° C.: | 78.1 | 60.2 |
| 300% Modulus @ 23° C. (MPa): | 9.8 | 7.1 |
| Tensile Strength @ 23° C. (MPa): | 14.3 | 10.3 |
| tan δ, 0° C., 0.5% E, 5 Hz: | 0.1572 | 0.1518 |
| tan δ, 50° C., 0.2% E, 5 Hz: | 0.2190 | 0.2431 |
| RDA 0.25–14% ΔG' (MPa): | 7.436 | 6.570 |
| tan δ, 50° C., 5.0% E, 1 Hz: | 0.2341 | 0.2707 |
| Bound Rubber (%): | 26.5 | 18.4 |

The data contained in Table XI demonstrates a 13.5% reduction in tan δ for the silica/carbon black reinforced compound containing the SBR polymer with the initiator DAPDT-Li (Ex. No. 32) as compared to the compound comprising the control polymer (Ex. No. 33).

Further examples were conducted and are reported as follows.

Example 34

Synthesis of Poly(styrene-co-butadiene) with 2-lithio-2-(4-dimethyl-amino)phenyl-1,3-dithiane Table XII below contains data characterizing the polymers resulting from three different methods of initiating the polymerization of an approximately 110 kg/mol $M_n$ butadiene and styrene copolymer in a two-gallon (7.6 L) reactor. Initiation No. 1 involved the direct addition of 2-lithio-2-(4-dimethyl-amino)phenyl-1,3-dithiane; Initiation No. 2 involved the addition of n-BuLi and 2-(4-dimethyl-amino)phenyl-1,3-dithiane together; and Initiation No. 3 involved the addition of 2-(4-dimethyl-amino)phenyl-1,3-dithiane and n-BuLi separately.

TABLE XII

| | Initiation Number | | |
|---|---|---|---|
| | 1 | 2 | 3 |
| $M_n$ (kg/mol) | 115.3 | 113.4 | 109.9 |
| $M_w/M_n$ | 1.09 | 1.08 | 1.35 |

Example 35

Synthesis of Poly(styrene-co-butadiene) with 2-lithio-2-(4-dimethyl-amino)phenyl-1,3-dithiane in-situ and Terminated with DMI To a two gallon (7.6 L) $N_2$ purged reactor equipped with a stirrer was added 1.610 kg of hexane, 0.412 kg of 33 weight % styrene in hexane, and 2.419 kg of 22.5 weight % butadiene in hexane. The reactor was then charged a mixture of 1.36 g of 2-(4-dimethylamino)phenyl-1,3-dithiane in 10 mL of THF and 1 mL of triethylamine with 3.37 mL of n-BuLi (1.68 M) in hexane, and agitated at 24° C. for 5 to 10 minutes, then 1.5 mL of 1.6 M in hexane was charged, and the reactor jacket was then heated to 50° C. After 16 minutes, the batch temperature peaked at 62.7° C. After an additional 15 minutes, the cement was removed from the reactor and placed in dried 28-oz (0.8 L) glass bottles, then terminated with the following: isopropanol (abbreviated as DAPDT-SBR-H) and 1,3-dimethyl-2-imidazolidinone (DMI, 9.14 M; abbreviated as DAPDT-SBR-DMI), at 50° C. bath for 30 minutes, then coagulated in isopropanol containing butylated hydroxy tolune (BHT), and drum dried to yield the polymers with following properties:

TABLE XIII

| | Example No. | |
|---|---|---|
| | 35A | 35B |
| Description | DAPDT-SBR-H | DAPDT-SBR-DMI |
| $M_n$ (kg/mol) | 108.5 | 68.7* |
| $M_w$ (kg/mol) | 117.6 | 75.0* |
| $T_g$ (° C.) | −29.7 | −29.9 |
| $ML_{1+4}$ @ 100° C. | 11.5 | 9.5 |

*apparent $M_n$ and $M_w$ are low due to interaction of polymer with GPC columns.

Example 36

Synthesis of Poly(styrene-co-butadiene) with n-BuLi

The preparation and the procedure used in Example 35 were repeated, and n-BuLi (1.68 M in hexane) was used as an anionic polymerization initiator. The polymers with the following properties are used as the control.

TABLE XIV

| | Example No. | |
|---|---|---|
| | 36A | 36B |
| Description | n-Bu-SBR-H | n-Bu-SBR-DMI |
| $M_n$ (kg/mol) | 110.6 | 97.1* |
| $M_w$ (kg/mol) | 114.8 | 100.5* |
| $T_g$ (° C.) | −29.9 | −29.9 |
| $ML_{1+4}$ @ 100° C. | 7.0 | 7.5 |

*apparent $M_n$ and $M_w$ are low due to interaction of polymer with GPC columns.

Application in Rubber Compounds

The SBR polymers prepared according to Examples 35–36 were utilized to prepare a vulcanizable elastomeric compound that contained carbon black as the reinforcing filler. The compound formulation used was the generic formulation shown in Table VII hereinabove. The results of physical testing are presented in Table XV.

TABLE XV

| | Compound Example No.: | | | |
|---|---|---|---|---|
| | 37 | 38 | 39 | 40 |
| | Polymer Example. No: | | | |
| | 36A | 36B | 35A | 35B |
| 171° C. MDR $t_{50}$ (min): | 3.11 | 1.99 | 3.04 | 1.93 |
| 171° C. MH-ML (kg-cm): | 17.3 | 16.5 | 20.9 | 19.3 |
| $ML_{1+4}$ @ 130° C.: | 24.3 | 37.8 | 29.2 | 42.4 |
| 300% Modulus @ 23° C. (MPa): | 10.92 | 14.39 | 12.87 | 15.61 |
| Tensile Strength @ 23° C. (MPa): | 15.37 | 15.75 | 15.42 | 16.93 |
| Tan δ, 0° C., 0.5% E, 5 Hz: | 0.2666 | 0.3425 | 0.2795 | 0.3516 |
| tan δ, 50° C., 0.2% E, 5 Hz: | 0.2770 | 0.1744 | 0.2508 | 0.1522 |
| RDA 0.25–14% ΔG' (MPa): | 4.67 | 0.51 | 4.09 | 0.55 |
| tan δ, 50° C., 5.0% E, 1 Hz: | 0.2710 | 0.1130 | 0.2244 | 0.0894 |

As can be seen in Table XV, compounding carbon black with the SBR polymer prepared in-situ with the initiator DAPDT-Li (Compound Example No. 39), provided a 17.2% reduction in tan δ at 50° C., compared to the compound containing the control polymer prepared with n-BuLi initiator (Compound Example No. 37). Likewise, the DAPDT-SBR-DMI containing compound (Compound Example No. 40) provided a 20.9% reduction in tan δ at 50° C., compared to the compound containing the control n-Bu-SBR-DMI polymer (Compound Example No. 38).

Application in Rubber Compounds

The SBR polymers (Examples 35A and 35B) prepared according to Example No. 35 were utilized to prepare a vulcanizable elastomeric compound with a combination of carbon black and silica as fillers, designated as Compound Example Nos. 41 and 42. For comparison, compounds containing the control polymers Example Nos. 36A and 36B) were prepared using the combination carbon black/silica formulation, and designated as Compound Example Nos. 43 and 44. The carbon black/silica formulation used for Compound Example Nos. 41–44 was the generic formulation shown in Table X hereinabove.

TABLE XVI

| | Compound Example No.: | | | |
|---|---|---|---|---|
| | 43 | 44 | 41 | 42 |
| | Polymer Example No.: | | | |
| | 36A | 36B | 35A | 35B |
| 171° C. MDR $t_{50}$ (min): | 7.27 | 5.02 | 6.46 | 3.84 |
| 171° C. MH-ML (kg-cm): | 22.15 | 17.81 | 24.81 | 21.67 |
| $ML_{1+4}$ @ 130° C.: | 53.9 | 91.1 | 69.9 | 100.7 |
| 300% Modulus @ 23° C. (MPa): | 8.3 | 10.9 | 10.0 | 13.4 |
| Tensile Strength @ 23° C. (MPa): | 12.2 | 14.9 | 14.4 | 16.6 |
| tan δ, 0° C., 0.5% E, 5 Hz: | 0.2602 | 0.2926 | 0.2665 | 0.3200 |
| tan δ, 50° C., 0.2% E, 5 Hz: | 0.2628 | 0.1980 | 0.2377 | 0.1744 |
| RDA 0.25–14% ΔG' (MPa): | 8.231 | 2.240 | 6.562 | 1.766 |
| tan δ, 50° C., 5.0% E, 1 Hz: | 0.2578 | 0.1743 | 0.2244 | 0.1318 |

As can be seen in Table XVI, formulating a silica/carbon black compound with a SBR polymer prepared in-situ with the initiator DAPDT-Li provided a 13% reduction in tan δ at 50° C., compared to the control compound containing the polymer prepared with n-BuLi initiator (Compound Example Nos. 41 and 43). The DAPDT-SBR-DMI containing silica/carbon black compound also provided a 24.4% reduction in tan δ at 50° C., compared to the n-Bu-SBR-DMI containing silica/carbon black compound (Compound Example Nos. 42 and 44).

Further examples were conducted to study the properties of terminated polymers according to the present invention having head and tail functionality.

Example 45

Synthesis of 2-lithio-2-methyl-1,3-dithiane Initiated Polymer

To a 19 L reactor was added 4.75 kg hexane, 1.25 kg 33% styrene in hexane, and 7.55 kg 21.7 wt % butadiene in hexane. Then, 37.1 mL of 0.5 M 2-methyl-1,3-dithiane in hexanes, 11.04 mL of 1.68 M butyl lithium in hexanes, and 3.83 mL of 1.6 M of a cyclic oligomeric oxolanyl alkane modifier in hexane were added. The batch was then heated to 48.9° C. After 22 minutes, the reactor jacket was flooded with cold water. After an additional 41 minutes, 3.08 kg of polymer cement was discharged from the reactor into isopropanol containing butyltated hydroxy toluene (BHT). The polymer was coagulated and drum dried and had the following properties: $M_n$=93.7 kg/mol, $M_w$=98.3 kg/mol, $T_g$=−31.3° C., % styrene=20.2, % block styrene=2.2%, % 1,2 butadiene=44.9%.

Example 46

Synthesis of 2-lithio-2-methyl-1,3-dithiane Initiated and tetraethylorthosilicate (TEOS) Terminated Polymer An additional 2.36 kg of cement prepared in Example 45 was removed under nitrogen from the reactor. This was terminated with 1 eq. of TEOS per BuLi. The resulting polymer was coagulated in isopropanol and drum dried to yield a polymer with the following properties: $M_n$=219 kg/mol, $M_w$=385 kg/mol, $T_g$−31.5° C., % styrene=20.6, % block styrene=2.0%, % 1,2 butadiene=45.6%.

Example 47

Synthesis of 2-lithio-2-methyl-1,3-dithiane Initiated and 2-methylthio-2-thiazoline Terminated Polymer An additional 2.21 kg of cement prepared in Example 45 was removed under nitrogen from the reactor. This was terminated with 1 eq. of 2-methylthio-2-thiazoline per BuLi. The resulting polymer was coagulated in isopropanol and drum dried to yield a polymer with the following properties: $M_n$ 111 kg/mol, $M_w$ 126 kg/mol, $T_g$ −30.9° C., % styrene 20.7, % block styene 1.9%, % 1,2 butadiene 45.5%.

Example 48

Synthesis of 2-lithio-2-methyl-1,3-dithiane Initiated and Tributyltin Chloride Terminated Polymer An additional 2.36 kg of cement prepared in Example 45 was removed under nitrogen from the reactor. This was terminated with 1 eq. of Bu$_3$SnCl per BuLi. The resulting polymer was coagulated in isopropanol and drum dried to yield a polymer with the following properties: $M_n$ 106 kg/mol, $M_w$ 113 kg/mol, $T_g$ −31.30° C., % styrene 21.0, % block styene 2.0%, % 1,2 butadiene 45.6%.

The foregoing polymers were compounded with carbon black following the generic formulation set forth in Table VIII (Compound Example Nos. 49–52) and with a mixture of silica/carbon black following the generic formulation set forth in Table X hereinabove (Compound Example Nos. 53–57). Next, the resulting compounds were cured and subjected to physical testing, as set forth in Tables XVII and XVIII below.

TABLE XVII

Carbon Black Formulation

| | Compound Example No. | | | |
|---|---|---|---|---|
| | 49 | 50 | 51 | 52 |
| | Polymer Example No. | | | |
| | 45 | 46 | 47 | 48 |
| ML$_{1+4}$ @ 130° C. | 18.7 | 61.9 | 34.2 | 27.8 |
| 300% Modulus @ 23° C. (MPa): | 9.69 | 12.34 | 12.53 | 11.48 |
| Tensile Strength @ 23° C. (MPa): | 13.51 | 15.65 | 15.08 | 14.84° |
| tan δ, 0° C., 0.5% E, 5 Hz: | 0.398 | 0.433 | 0.445 | 0.433 |
| tan δ, 50° C., 0.2% E, 5 Hz: | 0.285 | 0.229 | 0.209 | 0.229 |
| RDA 0.25–14% ΔG' (MPa): | 5.237 | 2.994 | 1.187 | 1.598 |
| tan δ, 50° C., 5.0% E, 1 Hz: | 0.282 | 0.210 | 0.149 | 0.176 |
| Bound Rubber (%): | 10.9 | 42.6 | 34.4 | 31.5 |

TABLE XVIII

Silica/Carbon Black Formulation

| | Compound Example No. | | | |
|---|---|---|---|---|
| | 53 | 54 | 55 | 56 |
| | Polymer Example No. | | | |
| | 45 | 46 | 47 | 48 |
| ML$_{1+4}$ @ 130° C. | 46.7 | 96.5 | 73.0 | 62.7 |
| 300% Modulus @ 23° C. (MPa): | 8.22 | 12.70 | 10.68 | 10.24 |
| Tensile Strength @23° C. (MPa): | 10.31 | 15.49 | 13.27 | 12.11 |
| tan δ, 0° C., 0.5% E, 5 Hz: | 0.348 | 0.415 | 0.386 | 0.382 |
| tan δ, 50° C., 0.2% E, 5 Hz: | 0.248 | 0.202 | 0.222 | 0.224 |
| RDA 0.25–14% ΔG' (MPa): | 8.028 | 3.732 | 4.358 | 5.170 |
| tan δ, 50° C., 5.0% E, 1 Hz: | 0.252 | 0.176 | 0.199 | 0.209 |

As can be seen in Tables XVII and XVIII, formulating carbon black and silica/carbon black reinforced SBR polymers prepared with the initiator 2-lithio-2-methyl-1,3-dithiane and then providing terminal functionality (Compound Example Nos. 50–52, 54–56) provided a reduction in tan δ compared to the polymer prepared with the initiator but not functionally terminated (Compounds Example Nos. 49 and 53).

Based upon the foregoing disclosure, it should now be apparent that the use of the anionic polymerization initiators described herein provides a useful method for the polymerization of diene and monovinyl aromatic monomers. As should be evident from the data provided in the tables herein, presence of the functional groups, according to the present invention, on polymers from which vulcanizable elastomeric compositions can be made can provide improved physical properties in various articles such as tires and the like, compared with the same polymers which do not carry these functional groups.

It is, therefore, to be understood that any variations evident fall within the scope of the claimed invention and thus, the selection of specific component elements can be determined without departing from the spirit of the invention herein disclosed and described. In particular, anionic polymerization initiators according to the present invention are not necessarily limited to those dithianes exemplified herein.

Various modifications and alterations that do not depart from the scope and spirit of this invention will become apparent to those skilled in the art. This invention is not to be duly limited to the illustrative embodiments set forth hereinabove. Thus, the scope of the invention shall include all modifications and variations that may fall within the scope of the attached claims.

What is claimed is:

1. A functional polymer that is defined by the following formula:

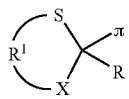

where R is selected from $C_1$ to $C_6$ trialkyl-silyl groups, $C_1$ to $C_{20}$ alkyl groups, $C_4$ to $C_{20}$ cycloalkyl groups, $C_6$ to $C_{20}$ aryl groups, thienyl, furyl, and pyridyl groups; and R may optionally have attached thereto any of the following functional groups: $C_1$ to $C_{10}$ alkyl groups, $C_6$ to $C_{20}$ aryl groups, $C_2$ to $C_{10}$ alkenyl groups, $C_3$ to $C_{10}$ non-terminal alkynyl groups, ethers, tert-amines, oxazolines, thiazolines, phosphines, sulfides, silyls, and mixtures thereof; where $R^1$ is selected from $C_2$ to $C_8$ alkylene groups, where X is sulfur, and where π is a polymer chain.

2. The polymer of claim 1, where said polymer chain derives from the anionic polymerization of monomer including conjugated dienes and optionally vinyl aromatics.

3. The polymer of claim 1, where said polymer chain includes poly(styrene-co-butadiene).

4. The polymer of claim 1, where said polymer chain includes a terminal functional group that includes a trialkyltin group, a thiazoline group, a trialkoxysilane group, or a carboxamide group.

5. The polymer of claim 1, where said polymer chain includes a terminal group resulting from the termination of said polymer chain with a reagent selected from the group consisting of tin tetrachloride, tributyltin chloride, dibutyltin chloride, tetraethylorthosilicate, 1,3-dimethyl-2-imidazolidinone, and mixtures thereof.

6. The polymer of claim 1, where R includes a $C_6$ to $C_{20}$ aryl group having attached thereto a tert-amine group.

7. A method for preparing a functional polymer, the method comprising:
contacting monomer including conjugated dienes with a sulfur-containing initiator to form a living polymer, where the initiator is defined by the formula

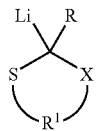

where R is selected from $C_1$ to $C_6$ trialkyl-silyl groups, $C_1$ to $C_{20}$ alkyl groups, $C_4$ to $C_{20}$ cycloalkyl groups, $C_6$ to $C_{20}$ aryl groups, thienyl, furyl, and pyridyl groups; and R may optionally have attached thereto any of the following functional groups: $C_1$ to $C_{10}$ alkyl groups, $C_6$ to $C_{20}$ aryl groups, $C_2$ to $C_{10}$ alkenyl groups, $C_3$ to $C_{10}$ alkynyl groups, ethers, tert-amines, oxazolines, thiazolines, phosphines, sulfides, silyls, and mixtures thereof; where $R^1$ is selected from $C_2$ to $C_8$ alkylene groups, and where X is sulfur.

8. The method of claim 7, where the monomer includes conjugated dienes and vinyl aromatics.

9. The method of claim 8, where said step of contacting takes place in a solvent.

10. The method of claim 9, further comprising contacting the living polymer with a terminating agent, a coupling agent, or a linking agent.

11. The method of claim 10, where the terminating agent is selected from the group consisting of tin tetrachloride, tributyltin chloride, dibutyltin chloride, tetraethylorthosilicate, 1,3-dimethyl-2-imidazolidinone, and mixtures thereof.

12. The method of claim 7, where the sulfur-containing initiator is defined by the formula

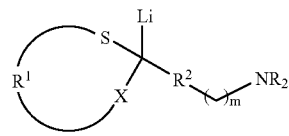

where R is selected from the group consisting of $C_1$ to $C_6$ trialkyl-silyl groups, $C_1$ to $C_{20}$ alkyl groups, $C_4$ to $C_{20}$ cycloalkyl groups, $C_6$ to $C_{20}$ aryl groups, thienyl, furyl, and pyridyl groups; where $R^1$ is selected from the group consisting of $C_2$ to $C_8$ alkylene groups; where $R^2$ is selected from the group consisting of $C_1$ to $C_8$ alkylene groups, $C_3$ to $C_{12}$ cycloalkylene groups and $C_6$ to $C_{18}$ arylene groups; where m is 0 to about 8, and where X is sulfur.

13. The method of claim 7, wherein the initiator is selected from the group consisting of 2-lithio-2-methyl-1,3-dithiane, 2-lithio-2-phenyl-1,3-dithiane, 2-lithio-2-(4-dimethylamino)phenyl-1,3-dithiane, 2-lithio-2-trimethylsilyl-1,3-dithiane, and 2-lithio-2-(4-dibutylaminophenyl)-1,3-dithiane.

14. A vulcanized rubber composition comprising:
the vulcanization product of a functional polymer, where the functional polymer is defined by the formula

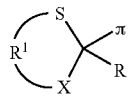

where R is selected from $C_1$ to $C_6$ trialkyl-silyl groups, $C_1$ to $C_{20}$ alkyl groups, $C_4$ to $C_{20}$ cycloalkyl groups, $C_6$ to $C_{20}$ aryl groups, thienyl, furyl, and pyridyl groups; and R may optionally have attached thereto any of the following functional groups: $C_1$ to $C_{10}$ alkyl groups, $C_6$ to $C_{20}$ aryl groups, $C_2$ to $C_{10}$ alkenyl groups, $C_3$ to $C_{10}$ non-terminal alkynyl groups, ethers, tert-amines, oxazolines, thiazolines, phosphines, sulfides, silyls, and mixtures thereof; where $R^1$ is selected from $C_2$ to $C_8$ alkylene groups, where X is sulfur, and where π is a polymer chain.

15. The vulcanized rubber of claim 14, where said polymer chain derives from the anionic polymerization of monomer including conjugated dienes and optionally vinyl aromatics.

16. The vulcanized rubber of claim 14, where said polymer chain includes a terminal functional group that includes a trialkyltin group, a thiazoline group, a trialkoxysilane group, or a carboxamide group.

17. The vulcanized rubber of claim 14, where said polymer chain includes a terminal group resulting from the termination of said polymer chain with a reagent selected from the group consisting of tin tetrachloride, tributyltin chloride, dibutyltin chloride, tetraethylorthosilicate, 1,3-dimethyl-2-imidazolidinone, and mixtures thereof.

18. The vulcanized rubber of claim 14, where the rubber composition further comprises a filler selected from the group consisting of carbon black, silica, starch, aluminum hydroxide, magnesium hydroxide, clays, and mixtures thereof.

19. The vulcanized rubber of claim 15, where R includes a $C_6$ to $C_{20}$ aryl group having attached thereto a tert-amine group.

20. A tire component comprising the rubber composition of claim 16.

* * * * *